United States Patent [19]

Kaltenbach et al.

[11] Patent Number: 4,705,668

[45] Date of Patent: Nov. 10, 1987

[54] ELECTROLYTE ANALYZER

[75] Inventors: Karl W. Kaltenbach, Newtonville; Stephen Rettew, Newton; John O. Rudy, Cambridge, all of Mass.; Gabor L. Szakacs, Nashua, N.H.

[73] Assignee: Medica Corporation, Bedford, Mass.

[21] Appl. No.: 900,784

[22] Filed: Oct. 14, 1986

Related U.S. Application Data

[62] Division of Ser. No. 716,670, Mar. 27, 1985, Pat. No. 4,649,028.

[51] Int. Cl.⁴ .................... G01N 35/08; G01N 27/26
[52] U.S. Cl. ...................... 422/82; 204/409; 422/68; 422/103; 436/53; 436/150
[58] Field of Search .................... 204/409, 410, 411; 422/81, 82, 100, 102, 103, 68; 436/53, 150

[56] References Cited

U.S. PATENT DOCUMENTS

| | | | |
|---|---|---|---|
| 3,520,470 | 7/1970 | Faust | 229/56 |
| 3,545,671 | 12/1970 | Ross | 233/26 |
| 3,943,929 | 3/1976 | Patel | 128/275 |
| 4,136,678 | 1/1979 | Beach | 123/1 R |

OTHER PUBLICATIONS

Orion Research Incorporated, *Instruction Manual*, Model 1020, *Sodium/Potassium Analyzer*, (1982), pp. 1-17.

Beedie, M., *Electronic Design*, (Jan. 10, 1985), pp. 91-92, "Purely Optical Switch Positions Itself for Fiber-Optic Telecomm".

Orion Biomedical, Division of Orion Research Incorporated, Instruction Manual Space-Stat 30, *Sodium/Potassium Analyzer*, (revised Feb. 1980), pp. 1-25.

Orion Biomedical, a division of Orion Research Incorporated, Instruction Manual Space-Stat 20, *Ionized Calcium Analyzer*, (revised, Jan. 1980), pp. 1-34.

*Primary Examiner*—Michael S. Marcus

*Attorney, Agent, or Firm*—Hamilton, Brook, Smith & Reynolds

[57] ABSTRACT

An analyzer for measuring the ionic values of electrolytes in a sample solution having a fluid flow-through air segment detector (300) and a plurality of fluid flow-through ion selective electrodes (97,98) for measuring the ionic values of electrolytes and a fluid flow-through reference membrane assembly (96) connected in series. There is also a reference electrode (95). There is a reservoir (77) containing an internal filling solution. The reference membrane assembly and the reference electrode are located in the reservoir and exposed to the internal filling solution.

A tubular fluid sampling probe (70) having a sampling port (63) aspirates air, sample and liquid reagents through the system.

The probe cooperates with a slide valve (64) having a passageway (53) through which the probe reciprocates. The passageway contains a plurality of chamber ports (46, 47, 48) each of which is sealed from the other ports by the tube sampling probe when its sampling port is positioned within a chamber port, A reagent pouch having a plurality of chambers communicating with a separate chamber port in the slide valve (20, 21) contains liquid reagents and a wash solution. One chamber in the reagent pouch receives waste and is in fluid communication with the flow-through reference membrane assembly.

Means (50) are employed for pumping an electrolyte sample in series through the probe, the air segment detector, the ion selective electrodes, the reference membrane, and then to the waste disposal chamber. There are electronic means for measuring the voltage signal generated between the selective electrode and the reference electrodes for calculating the ionic value of the electrolyte being measured.

13 Claims, 20 Drawing Figures

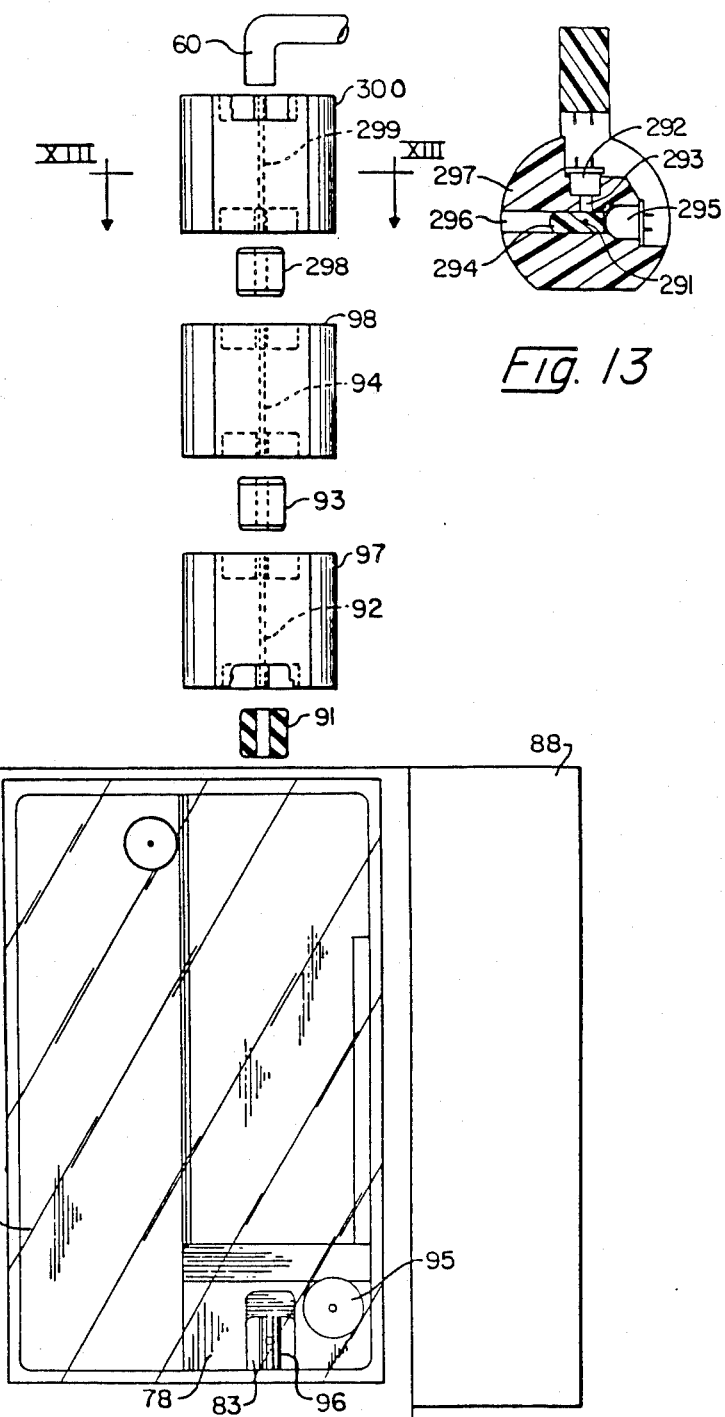
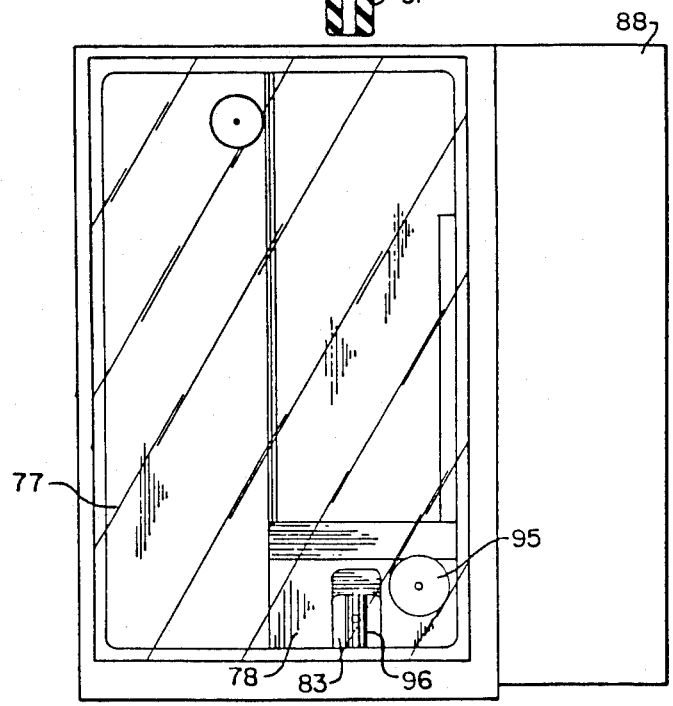
Fig. 13
Fig. 15

ELECTROLYTE ANALYZER

This application is a division of application Ser. No. 716,670, filed 3/27/85 now U.S. Pat. No. 4,649,028.

FIELD OF THE INVENTION

This invention relates to stat analyzers which determine the activity of electrolytes in solutions, and in particular, biological fluids.

BACKGROUND OF THE INVENTION

The first automated analyzers utilizing ion selective electrodes for measuring electrolytes in whole blood, plasma, or serum were developed in 1975 by Orion Research Incorporated. Orion's model SS-30 measured potassium and sodium, and its model SS-20 measured ionized calcium. Since that time, other analysers have been developed by Corning, Model 902; Instrumentation Laboratory, Models 501, 502, and 504, which are described in U.S. Pat. No. 4,283,262 granted Aug. 11, 1981, to Cormier et al. and U.S. Pat. No. 4,304,257, granted Dec. 8, 1981, to Webster; Nova Biomedical Corporation, Nova 1, 4, and 5; Kone OY, Microlyte; Radiometer, Model KNAI; Guilford Chemlyte NA/K; Beckman, Electrolyte 2 and System E4A; AVL Model 980; Dow Corning Direction 6000; Worthington, IE8200; and Photovolt 4M.

A most recent and advanced unit in the art is Orion's Model 1020. It does, however, have some limitations. First, it has separate bottles for its standardizing and maintenance solutions as well as a bottle to collect spent reagents and sample solutions. The operator is required to place different tubes in each bottle, and to change the bottles at different times. Orion's earlier model SS-30 utilized a cardboard fluids pack containing individual laminate reagent pouches and a plastic disposal bag into which separate plastic tubes were placed. Secondly, the Model 1020 requires manual operator interactive calibration procedures to adjust pumping to compensate for physical change in the peristaltic pump tubing. A third limitation is an expensive carriage assembly containing the ion selective electrodes, reservoir housing, and sample probe, all which have to be moved up and down when the analyzer aspirates a sample. The present invention overcomes these limitations.

The principal object of the invention is to provide a mechanically simple, low cost, user friendly, fully automated, electrolyte analyzer.

Another object is to provide an electrolyte analyzer with continuous and automatic pump tubing calibration.

Another object of the invention is to provide a stat electrolyte analyzer with a unique and automatic detection system for sensing bubbles or air segments, and for determining sample and reagent position.

Yet another object is to provide an electrolyte analyzer having an integrated reagent and waste disposal system.

SUMMARY OF THE INVENTION

The invention resides in an analyzer for measuring the ionic values of electrolytes in a sample solution and includes a fluid flow-through air segment detector and in a plurality of fluid flow-through ion selective electrodes for measuring the ionic values of electrolytes and in a fluid flow-through reference membrane assembly connected in series. Also included is a reference electrode and a reservoir containing an internal filling solution. The reference membrane assembly and the reference electrode are located in the reservoir and are exposed to the internal filling solution.

The analyzer includes a tubular fluid sampling probe which has one end closed and a sampling port spaced a finite distance from the closed end. The other end of the probe is in fluid communication with the air segment detector. The tubular fluid sampling probe cooperates with a slide valve which has a passageway in which the tube reciprocates. The passageway contains a plurality of chamber ports each of which is sealed from the other ports by the sampling probe when the sampling port is positioned within a chamber port.

The air segment or bubble detector has a detector body with a flow-through passage in the body through which the sample and various fluid reagents flow. There is a transverse passageway in the body which intersects the flow-through passage. A fiber optic is positioned in the transverse passageway intersecting the flow-through passageway. The fiber optic has a passageway which communicates with the flow-through passageway in the body and forms a continuous part thereof. A light source is positioned at one end of the transverse passageway aligned with the fiber optic to project light through the fiber optic. A light detector in the body is positioned transversely of the fiber optic and the flow-through passageway. By this mechanism, when two fluids or a fluid and air having different indices of refraction pass consecutively through the fluid passageway in the fiber optic, a change in the amount of light reflected from the fiber optic is detected by the light detector. A pump is employed for pumping a sample in series through the probe, the bubble or air segment detector, the ion selective electrodes, the reference membrane, and thence to a waste disposal chamber.

Electronic means are employed for measuring the voltage signal generated between the ion selective electrode and the reference electrode for calculating the ionic value of the electrolyte being measured.

The waste disposal chamber is located in a reagent pack which contains a pair of relatively flat, flexible pouches with sealed perimeters. The pouches are substantially equal size in volume and each pouch has a plurality of separate sealed compartments. One compartment is for the disposal waste, and the other compartments contain various fluid reagents and a wash solution.

A fitment is sealed to each pouch. The pouches are disposed in a sealed reagent pack with their perimeters and the fitments in juxtaposition. A tube which is in fluid communication with each compartment projects from the juxtaposition fitments outwardly of the pack. The centers of the tubes are arranged as the corners of a parallelogram.

Each chamber port in the slide valve communicates via a passageway with an opening in the face of the slide valve. The center of the openings in the slide valve and the tubes projecting from the reagent pack are arranged as the corners of a parallelogram of equal size to permit the tubes to mate with the openings in the slide valve in fluid communication.

A check valve is located in each passageway between the chamber ports and the openings in the face of the slide valve.

The above and other features of the invention including various novel details of construction and combinations of parts will now be more particularly described with reference to the accompanying drawings and pointed out in the claims. It will be understood that the particular electrolyte analyzer embodying the invention is shown by way of illustration only and not as a limitation of the invention. The principles and features of this invention may be employed in varied and numerous embodiments without departing from the scope of the invention.

BRIEF DESCRIPTION OF THE DRAWINGS

FIG. 13 is a sectional view of the bubble detector taken on the line XIII—XIII of FIG. 15.

FIG. 15 is an exploded front elevation of the reservoir housing and the electrodes and bubble detector contained therein.

BEST MODE OF CARRYING OUT THE INVENTION

General Organization

Figure 17:
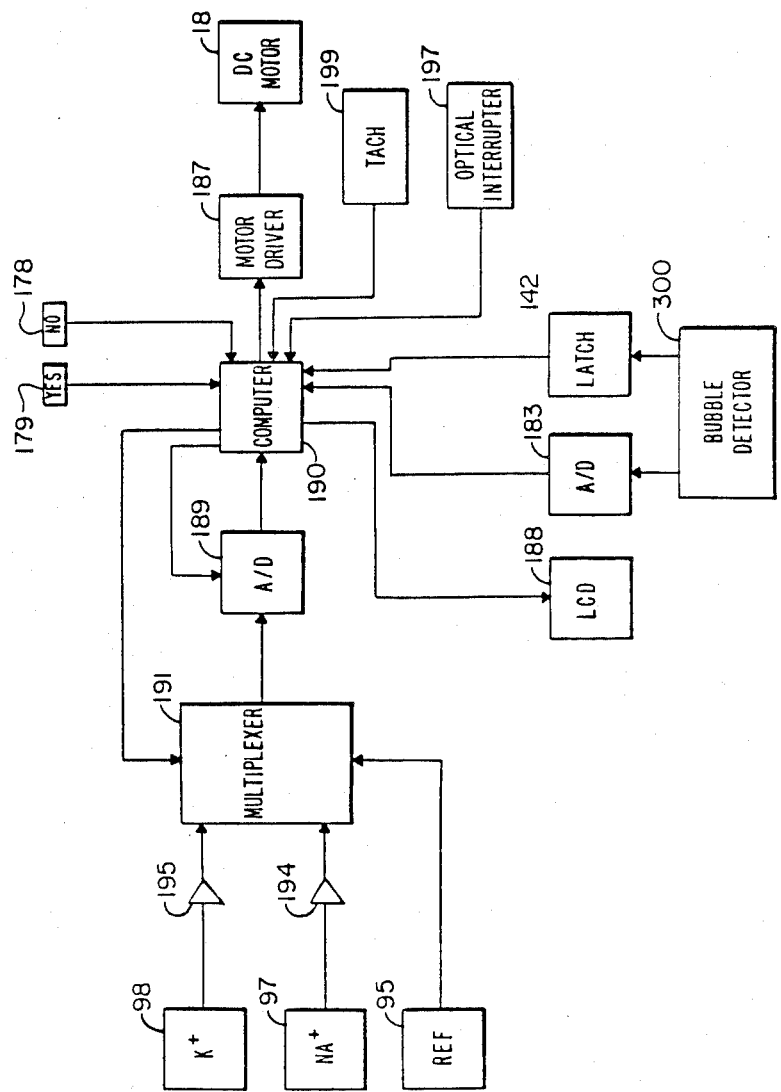
FIG. 17 is a component block diagram.

The invention is embodied in a stat electrolyte analyzer for measuring electrolytes in solution. In general, the analyzer has ion selective electrodes 97, 98 (FIGS. 15 and 17) for sensing elements; a bubble detector 300 (FIGS. 2, 13, and 15) for sensing air bubbles or segments of air; a sampling probe 70 (FIGS. 1 and 2) for aspirating fluid samples or reagents; a peristaltic pump 55 (FIGS. 1, 2, and 18) for moving fluid samples, reagents and air segments through the sampling probe 70, thence, past the bubble detector 300 and electrodes 97, 98, and into a waste disposal pouch 32 (FIG. 12); a DC motor 18 and two way clutch 17 (FIG. 18) for driving the peristaltic pump 55 and a cam 14 which, in turn, operates the sampling probe 70 via two linking arms 7 and 12; operational amplifiers 194 and 195 (FIG. 17) for buffering the voltage signals generated by the ion selective electrodes 97, 98; an analog multiplexer 191 for selecting signals; an A to D converter 189 for converting the signals into the digital domain; a microprocessor based computer 190 for controlling the mechanical functions of the analyzer and for computing the activity of the electrolyte to be measured; a digital display 188 for showing results and displaying messages and questions; reagent pouches 30 and 32 (FIGS. 11 and 12) containing standard solutions for calibrating the electrodes; reagent pouch 31 containing maintenance solution; a waste disposal pouch 30 for spent sample and reagent solutions; a reagent pack 20, 21 containing the pouches; a slide valve 64, which serves as an interface between the reagent pack and sample probe; and an analyzer housing 100 in which all the aforesaid components are assembled.

The Analyzing & Detecting Elements

Figure 2:
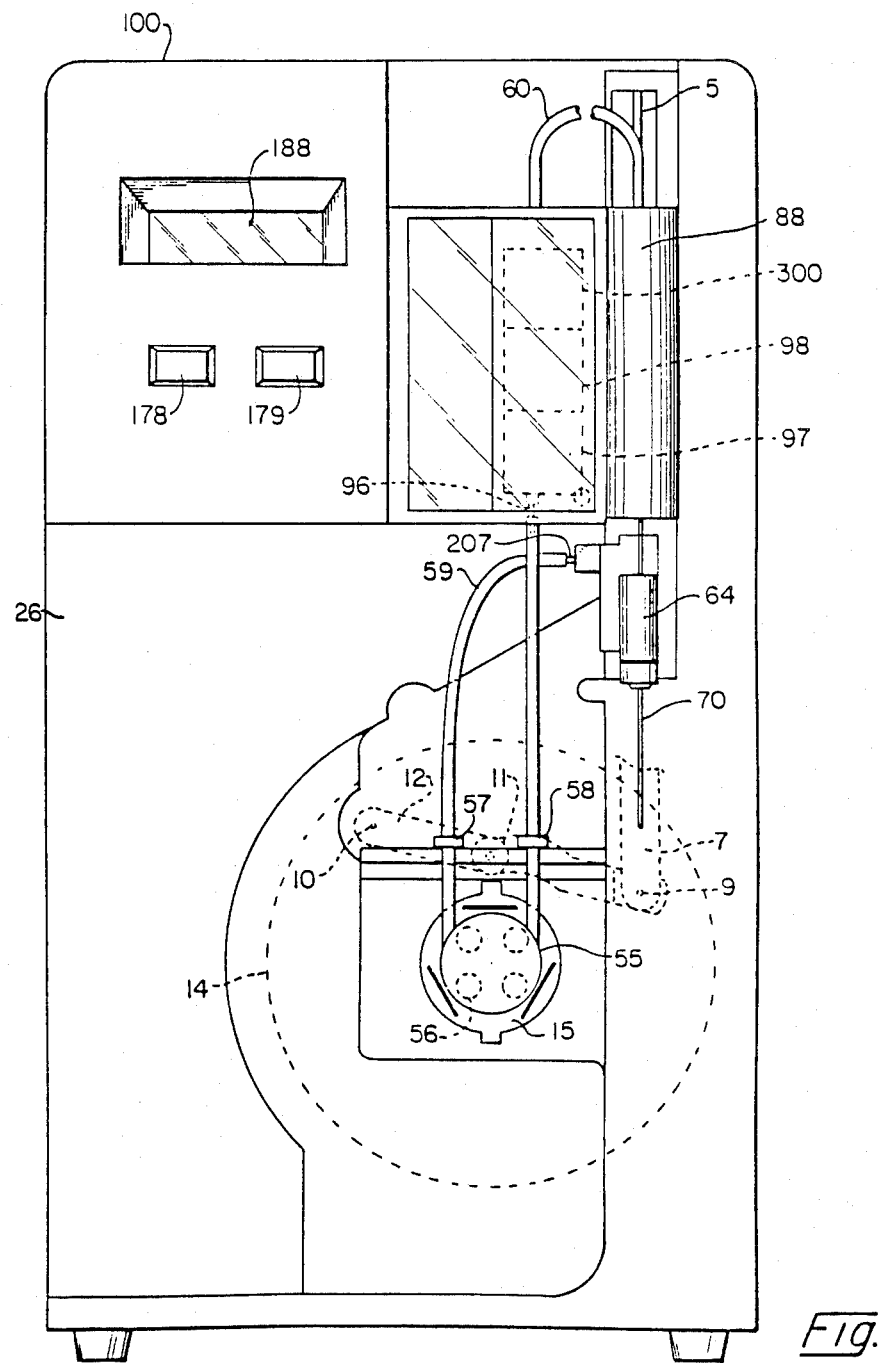
FIG. 2 is a front elevation of the analyzer.
Figure 14:
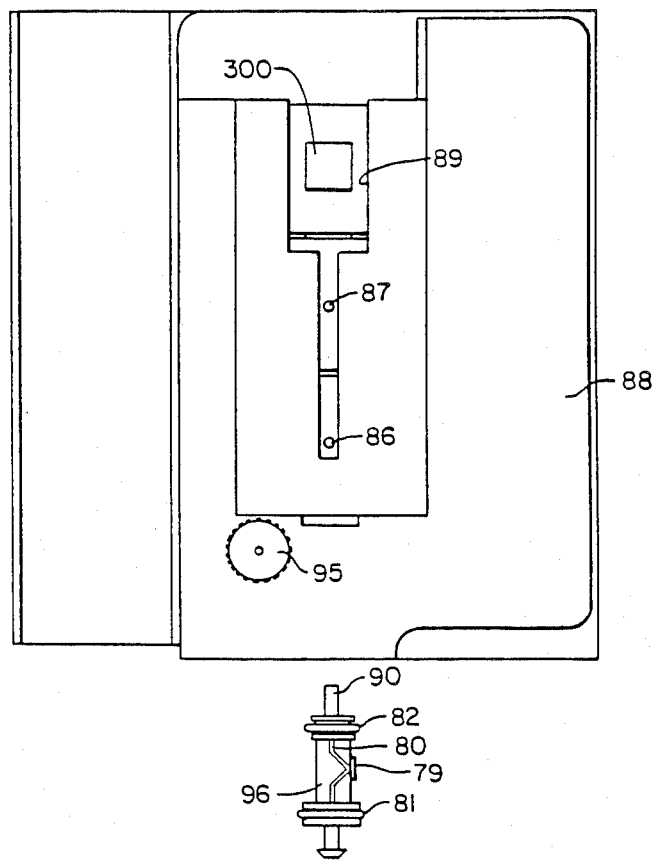
FIG. 14 is an exploded rear elevation of a reservoir housing and a reference membrane contained therein.

There will be seen in FIGS. 2 and 15, the flow-through bubble detector 300, the flow-through potassium ion-selective electrode 98 which has a membrane containing valinomycin, and the flow-through glass sodium electrode 97. A flow-through reference membrane assembly 96, and a silver/silver chloride reference electrode 95 are seen in FIG. 14.

A flow-through tube 299 (FIG. 15) of the bubble detector 300 is connected via flexible coupling 298 to the flow-through tube 94 of the potassium electrode 98 which, in turn, is connected via flexible coupling 93 to the flow-through tube 92 of sodium electrode 97 which, in turn, is connected via flexible coupling 91 to the flow-through tube 90 (FIG. 14) in the reference membrane assembly 96.

The potassium and sodium electrodes 99, 97 are mounted in a guide track 89 (FIG. 14) of a detachable reservoir housing 88. The electrical pins 86, 87 of the potassium and sodium electrodes 97, 98 are perpendicular to the cylindrical axis of the guide track 89 and the flow-through tubes 92, 94 of the electrodes 97, 98. They extend beyond the backside of the reservoir housing 88 and plug into electrical jacks 84, 85 (FIG. 3) in the analyzer housing 100. As such, the pins 86, 87 and electrodes 97, 98 help support the reservoir housing 88.

The bubble detector 300 is also mounted in the guide track 89, and plugs into an electrical connector 205 (FIG. 3) which also serves to support the reservoir housing 88. The bubble detector 300 is at the top of the guide track 89, and close to the top of the reservoir housing 88. The potassium electrode 98 is below the bubble detector 300, and the sodium electrode 97 rests in the bottom of the guide track 89.

The Reference Membrane Assembly

The reference membrane assembly 96 (best seen in FIG. 14) is cylindrical and fits into a cylindrical cavity 83 (FIG. 15) in the bottom of the reservoir housing 88. It is held in place by O-rings 81, 82 positioned near each of its ends. They form a watertight fit with the cylindrical cavity 83. The cylindrical axis of cavity 83 is aligned with the axis of the flow-through tubes 94, 92 of the potassium and sodium electrodes 98, 97. The reference membrane 96 assembly has a flow-through tube 80, the center section of which is of V shape and extends to the outer cylindrical wall of the assembly. Its upper end is connectable with the lower end of the flow-through tube 92 of the sodium electrode 97 via coupling 91 (FIG. 15). A portion of the cylindrical wall of the assembly is cut away where it is intersected by the V shaped portion of the flow-through tube 80. A cellophane membrane 79 is secured to the outside cylindrical wall of the reference membrane assembly 96 and covers the opening in the outside wall where it is intersected by the V shaped portion of the flow-through tube 80. The diameter of that portion of the reference membrane assembly 96 between its ends and containing the cellophane membrane 79 is less than the diameter of the cavity 83 so that the cellophane membrane 79 is not damaged when replacement reference membrane assemblies 96 are installed in the reservoir housing 88.

The cylindrical cavity 83 (FIG. 15) into which the reference membrane 96 fits is connected by means of an open portion 78 to a reservoir cavity 77 in the reservoir housing 88. It contains a 2 molar KCl reference solution, whereby the cellophane membrane 79 is surrounded by the reference solution. The pressure created by the head of reference solution assures a positive flow of that solution through the cellophane membrane 79 whereby contamination and clogging of the membrane 79 by the sample solution is reduced. The reference membrane assembly 96 is positioned farthest from the potassium electrode 98 to prevent possible contamination of the valinomycin membrane by the reference solution.

The Reference Electrode

Figure 16:
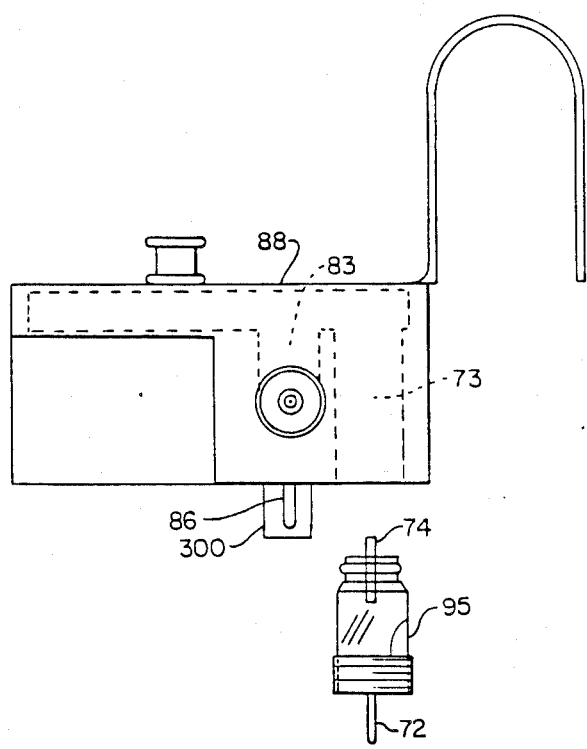
FIG. 16 is an exploded bottom view of the reservoir housing and the reference electrode contained therein.

The reference electrode 95 (FIG. 16) is a silver/silver chloride reference electrode. It contains an internal KCl filling solution and a ceramic frit 74. The reference electrode 95 is secured in a cylindrical cavity 73 in the backside of reservoir housing 88 by screw threads on its outer end. The cylindrical cavity 73 communicates with the reservoir cavity 77. The inner end of reference electrode 95 has an O-ring seal which forms a water tight fit with the cylindrical wall of cavity 73 and, as such, forms a seal with respect to the reference solution contained in reservoir cavity 77. This end also contains the ceramic frit 74 which is exposed to the reference solution 76 whereby an electrical connection is completed between the sample solution passing through the reference membrane assembly 96, the reference solution and the reference electrode 95.

The reference electrode 95 has an electrical pin 72 which extends beyond the backside of the reservoir housing 88 and which fits into electrical jack 71 (FIG. 3) in the analyzer housing 100. It serves as the principal support to the reservoir housing 88 which can be installed or removed from the analyzer housing 100 by simply plugging or unplugging pins 86, 87, and 72. The concentration of the KCl reference solution 75 in the reference electrode 95 is 2 molar KCl to minimize the liquid junction potential.

The Bubble Detector

The flow-through air segment or bubble detector 300 is illustrated in detail in FIG. 13. The body 297 of the detector 300 contains a horizontal cylindrical cavity 296 which passes through, and is perpendicular to, the vertical cylindrical axis of the detector body 297. Disposed in one end of the cavity 296 is a LED light source 295. A fiber optic 294 is disposed in the center section of the cavity 296. The fiber optic 294 has a diameter of about 0.125 inches and it is cemented in the cavity 296. Light from the LED 295 passes through the fiber optic 294 and out the opposite end of cavity 296. Perpendicular to cavity 296 is a horizontal cylindrical cavity 293 having a diameter of about 0.20 in. and which intersects, and ends at, the center section of cavity 296. Disposed in the outer end of cavity 293 is light detector 292.

The flow-through tube 299 of the detector 300 is comprised of a vertical cylindrical cavity passing through the vertical center axis of body 297. It is perpendicular to, and passes through, the fiber optic 294. The diameter of the cavity is about 0.030 in. The operation of the bubble detector will be described in greater detail hereinafter.

The Sample Probe

Figure 1:
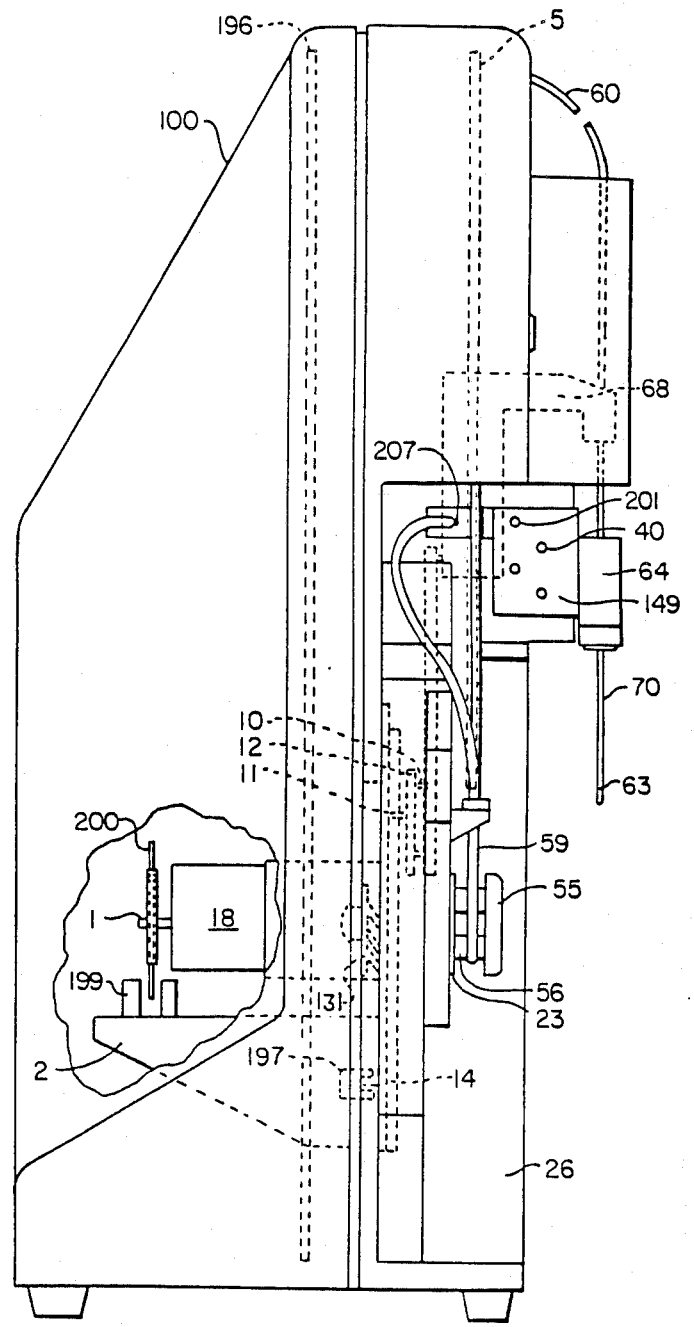
FIG. 1 is a side elevation of an electrolyte analyzer embodying features of the present invention.

The upper end of the tubular sample probe 70 is attached to a probe guide arm 68 (FIG. 1). The middle and lower end of probe 70 pass through, and are guided by a slide valve 64. The sample probe 70 has an outside diameter of 0.049 in. and an inside diameter of 0.034 in. The probe 70 also has a side port 63 which is located ¼ in. from its bottom end and has a diameter of approximately 0.031 in. The lower end of the probe is closed by a solid plug. The sampling port 63 interfaces with the ports in the slide valve 64 as will be more fully described hereinafter.

The upper end of probe 70 is connected to the bubble detector 300 by flexible tubing 60 having an inside diameter of 0.039 in. The length of the tubing 60 is about 6 ¼ in. and flexes sufficiently to permit the probe 70 to travel up and down through the slide valve 64. As noted above, the flow-through tubes 299, 94, 92, and 90 of the bubble detector 300, potassium electrode 98, sodium electrode 97, and the reference membrane assembly 96, respectively, are connected together by flexible couplings 298, 93, and 91, so that a continuous fluid path is formed from sampling port 63 in the probe 70 through the reference membrane assembly 96. The total volumetric displacement of the fluid path from port 63 of probe 70 to the bottom of the reference membrane assembly 96 is approximately 250 microliters.

The Peristaltic Pump

Flexible tubing 59 (FIG. 1) is connected to the bottom end of the reference membrane assembly 96, and passes tightly around rollers 56 of peristaltic pump 55 to a male fitting 207 on the slide valve 64. The tubing 59 has an inside diameter of 0.081 in. and is attached to the analyzer housing 100 at two points 57, 58 before and after the tubing 59 passes around the pump 55 so that the form of tubing 59 around the pump 55 is U-shaped and contacts approximately 180 degrees of the pump 55. When the pump 55 is rotated, the tubing 59 is compressed by the pump rollers 56. The point of compression travels in the direction of rotation of the pump 55 and at the speed of rotation of the pump 55. Fluid or air contained in the tube 59 is displaced ahead of the point of compression and a vacuum is created in the tube 59 behind the point of compression.

The Slide Valve

Figure 6:
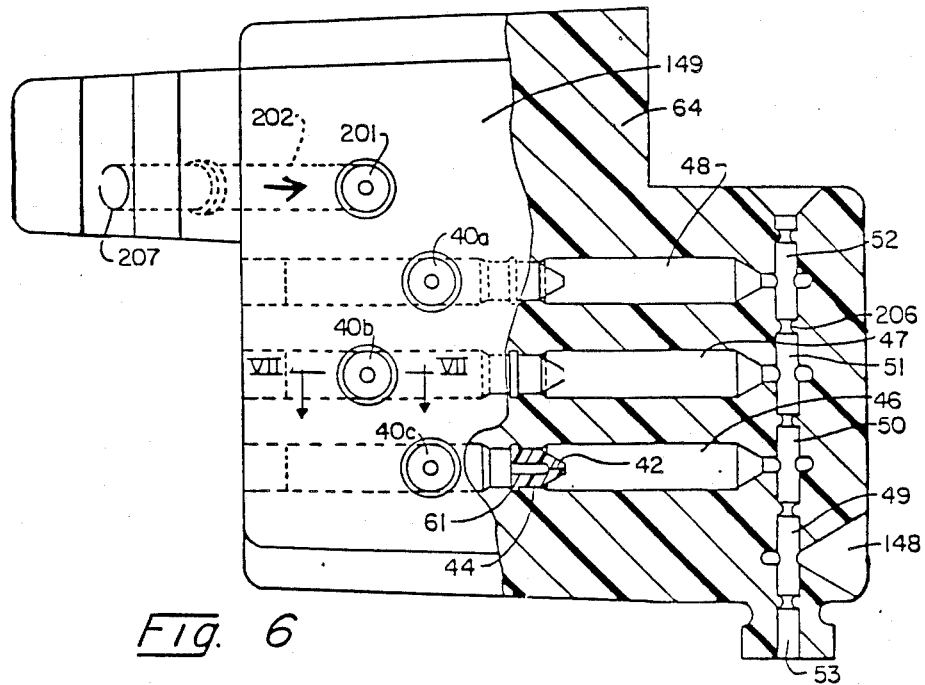
FIG. 6 is a side elevation, partly in section of a slide valve employed in the analyzer.
Figure 7:
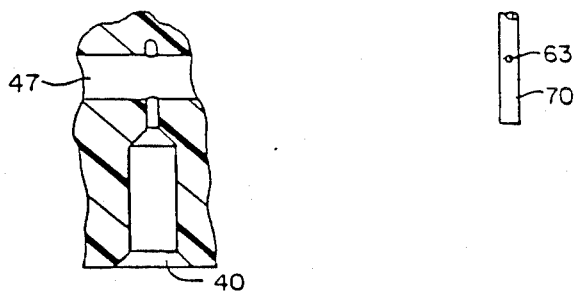
FIG. 7 is a sectional view taken on the line VII—VII on FIG. 6.

The slide valve 64 is best seen in FIGS. 6 and 7. It has a vertical cylindrical cavity 53 having a diameter of 0.062 in. and through which the probe 70 reciprocates. The cylindrical cavity 53 contains four chamber ports 49, 50, 51, and 52 which are equally spaced apart. The upper three ports 50, 51, and 52 communicate with three parallel channels, 46, 47, 48, which are perpendicular to the vertical axis of cavity 53. The channels 46, 47, 48, terminate at openings 40a, 40b, and 40c on one face 149 of the slide valve 64 which will be described in greater detail hereafter.

Port 49 is vented to atmosphere by opening 148. The chamber ports 49, 50, 51, 52 are approximately 0.062 in. in diameter and 0.18 in. in length. They are approximately 0.250 in. from each other. Neck portions 206 are located between the ports and have radii of 0.018 in. The cross section at the narrowest point of the cavity 53 is about 0.038 in.

The slide valve 64 is made of elastomeric material such as rubber, butyl, or silicones whereby the sections 206 of the cylindrical cavity 53 between chamber ports 49, 50, 51, 52 squeeze the probe 70 as it passes through them so that an air and liquid tight seal is formed between the chamber ports 49, 50, 51, and 52 and the probe 70. The necked portions 206 thus function as O-rings. Since the distance between centers of the chamber ports is 0.25 in. and since the side port 63 of probe 70 is approximately ¼ in. from its bottom end 65, each of the chamber ports 49, 50, 51, and 52 is sealed from the others when side port 63 of the probe 70 is aligned with one of the ports 49, 50, 51, and 52.

Each of the three channels 46, 47, 48 contains a duck bill type check valve 44. The valves are made of soft rubber. They are cylindrical near one end with a cylindrical ring 61 at the end, and are tapered to a fine slit 42 on the other end. Each of the channels 46, 47, 48 has a cylindrical slot into which the cylindrical ring 61 seats and whereby the check valve 44 is held in place in the channel. Air or liquid entering the cylindrical end, i.e. from left to right as seen in FIG. 6 expands the tapered end 42 such that the flow opens the slit 42 whereby the air or solution passes through the check valve 44. On the other hand, fluid going in the opposite direction tends to compress the tapered end and hence, the fine slit 42, whereby no fluid passes through the valve 44 in that opposite direction.

The slide valve 64 also contains a V shaped channel 202 which has the male fitting 207 at one end onto which tubing 59 connects (see FIG. 2). Tubing 59 communicates with the flow-through tube of the reference membrane assembly 96. Channel 202 terminates in an opening 201 on the same face 149 as openings 40a, 40b, and 40c. These openings are arranged in a predetermined geometric pattern.

It will be seen in FIG. 6 that the openings 40a and 40c in the slide valve 64 are in vertical alignment. The openings 201 and 40b are also in vertical alignment but spaced laterally from the openings 40a and 40b. The openings 201 and 40b are located higher on the slide valve 64 than the openings 40a and 40c, respectively. The centers are thus located at the corners of a parallelogram. A parallelogram is shown for illustrative purposes. Other predetermined geometric patterns may also be employed.

Figure 8:
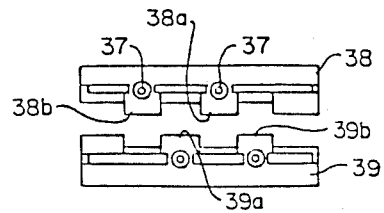
FIG. 8 is a detail view of interlocking fitments of the reagents and waste disposal pouches.

The openings 40a, 40b, 40c, and 201 function as receptacles to wedge shaped fitments 38 and 39 (FIGS. 8 and 12 and 20) which act as an interface between the slide valve 64 and the reagent pack 26. The fitments 38 and 39, each have two rigid tubes passing through them designated 37, 37a, 37b, and 37c. One end of each tube fits into openings 40a, 40b, and 40c, and the opening 201 in slide valve 64 as is explained more fully below. There is a slight shoulder or barb (FIG. 20) near the end of each tube 37 which causes a water tight fit when the tube 37 is pushed into the openings in the slide valve 64. The centers of tubes 37, 37a, 37b, and 37c projecting from the reagent pack are also arranged in a geometric pattern of the same size and slopes as the openings in the slide valve (See FIGS. 19 and 20). The dimensions of the parallelograms are identical to assure that the tubes 37, 37a, 37b, and 37c fit into the openings 201, 40a, 40b, and 40c respectively.

Reagent Pouches

Figure 11:
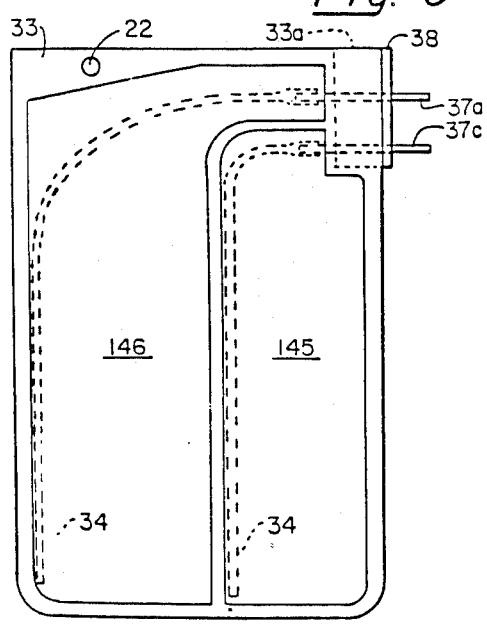
FIG. 11 is a front elevation of the reagent pouch.
Figure 12:
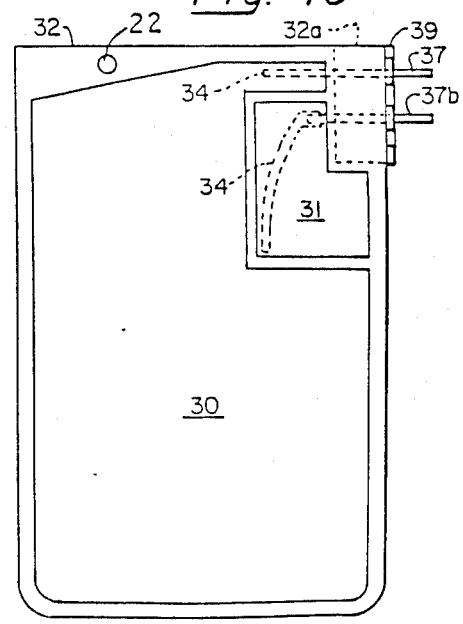
FIG. 12 is a front elevation of the waste disposal pouch.

The other end of the tubes 37 fit into flexible tubes 34, which are disposed in reagent pouches 32 and 33 (see FIGS. 11 and 12). Each pouch 32, 33 is made of two equal substantially rectangular, flat pieces of foil laminate which are heat sealed together at their perimeters to render them hermetically and fluid tight. Each pouch, 32, 33 has two compartments which are also formed by heat sealing a dividing line between them. The pouches 32, 33 being made out of foil, prevent evaporation of the reagents contained therein. In pouch 33, one compartment 145 has a capacity of about 130 ml and intended to contain Standard B, and a second compartment 146 is intended to contain about 400 ml of Standard A. In pouch 32, there is one small compartment 31 which can contain about 15 ml of daily wash or maintenance solution. The remainder 30 of pouch 32 serves as a waste disposal compartment for receiving spent sample solutions and reagents.

Each pouch 33, 32 has an opening 33a and 32a which is sealed to the wedge surfaces 38a and 39a of the fitments 39, 38 to form a permanent air tight seal between the pouches 33, 32 and the fitments 38, 39. Each flexible tube 34 is also sealed from the other, and each compartment in a pouch is sealed from the other compartment. The flexible tubes 34 run to the bottom of each pouch compartment to insure accessibility to all of the reagents contained therein. In the case of the waste disposal compartment 30, the tube 34 need only be of sufficient length to connect to the top of the compartment 30.

Reagent Pack

Each fitment 38, 39 has interlocking fingers 38b and 39b to enable the fitments to be snapped together and held in place as an integral part. The reagent pouches 32, 33 are of substantially the same size and have substantially the same internal volume are joined by the fitments 38, 39, lie side by side in parallel and are contained in the rectangular reagent pack 26.

Figures 9, 10:
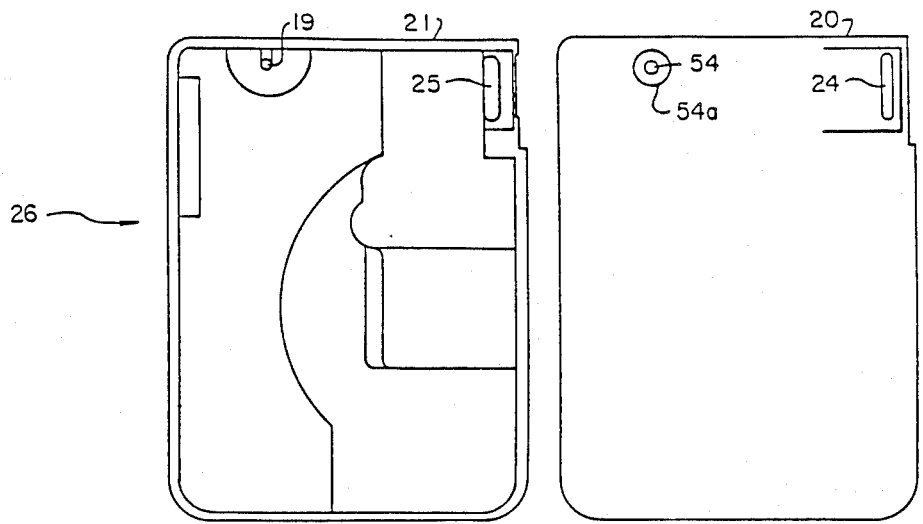
FIG. 9 is a rear elevation of the reagent pack employed in the analyzer.
FIG. 10 is a front elevation of the reagent pack.
Figure 19:
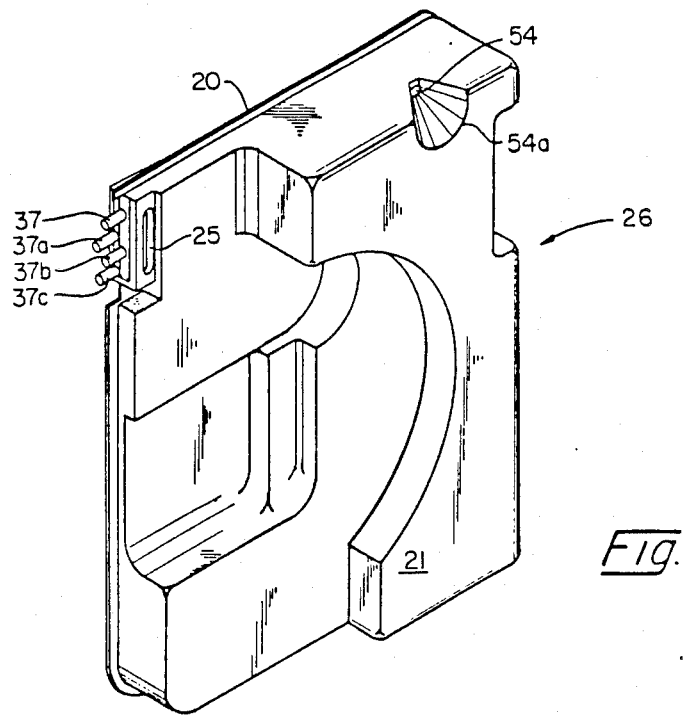
FIG. 19 is a rear perspective view of the reagent pack.
Figure 20:
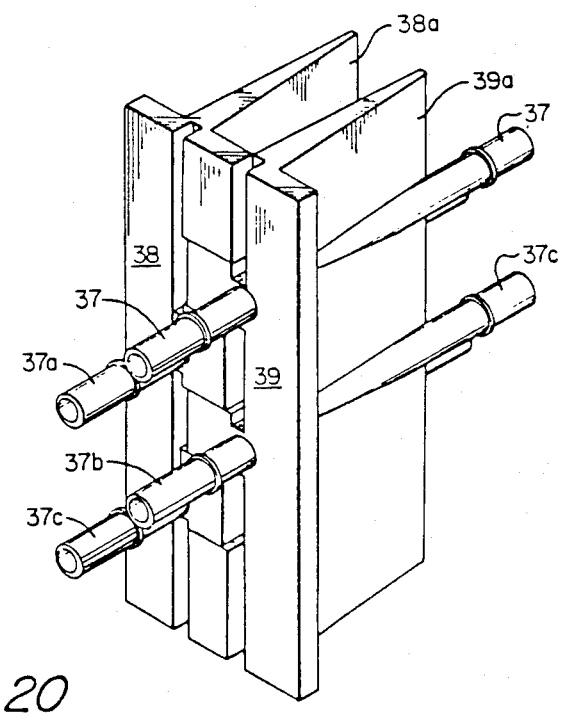
FIG. 20 is a perspective view, on enlarged scale, of the fitments of the reagent pack.

The reagent pack 26, shown in FIGS. 9, 10, and 19 is made of two high impact polystyrene halves, 20, 21. The back half 20 is contoured in a pattern that mates with contours of the analyzer housing 100 and peristaltic pump 55 which project outwardly through the front side of the analyzer housing 100 as seen in FIG. 1. The front half 21 of the pack has a flat surface which is flush with the analyzer housing 100 when the pack is in place. The perimeters of the pack halves 21, 20 match and contain slot receptacles 24, 25 which engage the fitments 38, 39 and hold them in place. The perimeters of the pack halves 20, 21 are bonded together to form a permanent closure.

The reagent pouches 32, 33 are secured inside the reagent pack 26 by a support post 19 projecting inwardly from in the back pouch half, 21. A hole 22 in the sealed perimeter trim of each pouch half 20, 21 is placed over the support post 19 and supported thereby. There is an inwardly projecting tapered indentation 54 in the front pack half 20 which mates with the support post 19. A conical indentation 54a in the outer surface serves as a finger hold for gripping the reagent pack 26 when the operator installs it into the analyzer by plugging the fitments 38, 39 into receptacles 40, 40a, 40b, and 201, of slide valve 64. The bottom of the reagent pack 26 is supported by the analyzer housing 100.

The Peristaltic Pump and Drive Mechanism

Peristaltic pump 55 is driven by a 24 volt D.C. gear motor 18. The pump 55 is mounted on the front half of a two-way cylindrical clutch 17 (FIG. 18) which is mounted on the output shaft 16 of the D.C. gear motor 18. The pump housing 23 is surrounded by a pump shield 15 (FIG. 2) which is mounted in the analyzer housing 100 by means of a snap fit. The shield is made of elastomeric material and fits snugly against the pump housing 23. It acts as a brake to prevent backturning of the pump when the back half of the two-way clutch 17 is rotating in the opposite direction.

Figure 4:
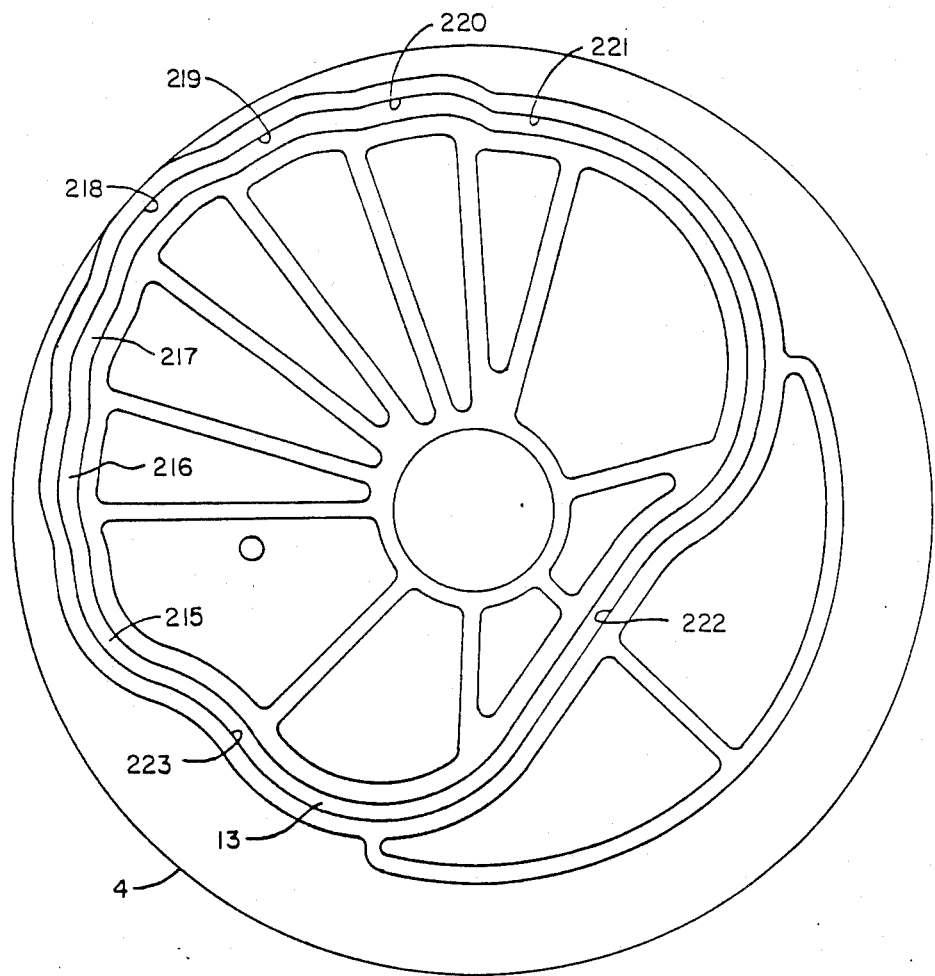
FIG. 4 is a front view of a cam employed in the analyzer.
Figure 5:
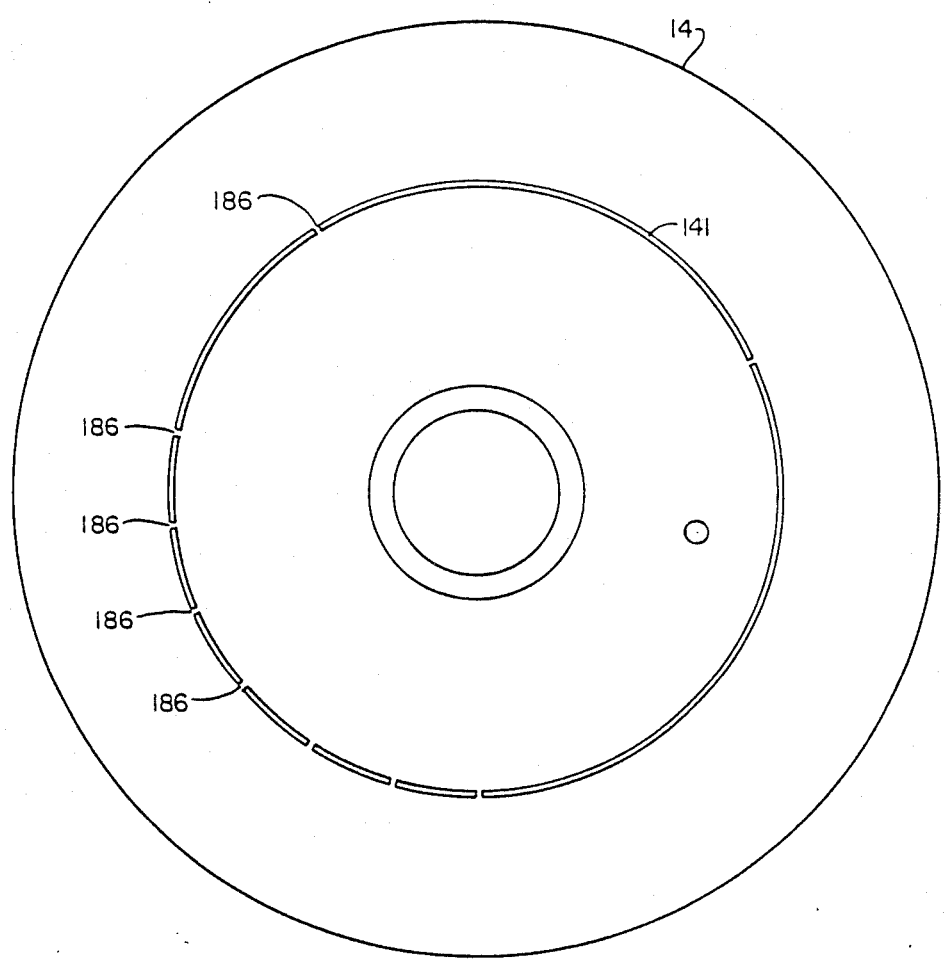
FIG. 5 is a rear view of cam of FIG. 4.

A cam 14 (shown in detail in FIGS. 4 and 5) is mounted on the back half of the two-way clutch 17 and rotates in the opposite direction to the peristaltic pump 55. The cam has a continuous groove or slot 13 on its circular disc face which varies in distance from the center of the cam as a function of the angle of rotation over 360 degrees. The cam 14 drives a front link arm 12 (seen best in FIGS. 1, 2, and 3). It is approximately 4.2 in. in length. One end of link arm 12 is attached by a pivot joint 10 to analyzer housing 100 about which it is free to rotate. The link arm 12 has a cam follower pin 11 intermediate of its ends and which is located about 1.9 inches from the pivot point 10. The diameter of the pin 11 is just slightly less than the width of slot 13, which is about 0.13 in. The other end of link arm 12 is attached by a pivot joint 9 to one end of a second link arm 7. The opposite end of the second link arm 7 is attached to the probe guide arm 68 by pivot joint 6. The probe arm 68 is constrained to move vertically by a vertical rod 5 which passes through a hole in probe arm 68. Rod 5 is attached to the analyzer housing 100 at both of its ends. The displacement of the probe guide arm 68 is equal to the vertical displacement of cam follower pin 11 times the distance between pivot point 10 and pivot point 9, divided by the distance between pivot point 10 and cam follower pin 11. As the cam 14 is rotated by the DC motor 18, the probe arm 68 glides up and down vertical rod 5, and hence probe 70 is also displaced vertically.

Operation of the Cam-driven Probe

The slot 13 in cam 14 is divided into 9 segments 215 to 223 (FIG. 4), a portion of each of which has a constant radius. These portions correspond to 9 positions of the probe 70 which are sequenced in the order set forth in Table No. 1 together with a description of the corresponding function performed by the analyzer at each position:

TABLE 1

| Position of Cam 14 | Description of Function |
| --- | --- |
| 215 | 215 |
| Probe 70 in lowest chamber port 49 of slide valve 64 | Pump 55 aspirates air through channel 148 in slide valve 64 |
| 216 | 216 |
| Probe 70 in next to lowest chamber port 50 of slide valve 64 | Pump 55 aspirates STD "B" from compartment 145 of pouch 33 |
| 217 | 217 |
| Probe 70 in next to highest chamber port 51 of slide valve 64 | Pump 55 aspirates daily wash solution from compartment 31 of pouch 32 |
| 218 | 218 |
| Probe 70 in highest highest chamber port 52 of slide valve 64 | Pump 55 aspirates Standard "A" from the compartment 146 of pouch 33 |
| 219 | 219 |
| Probe 70 in next to highest chamber port 51 of slide valve 64 | Pump 55 aspirates daily wash solution from compartment 31 of pouch 32 |
| 220 | 220 |
| Probe 70 in next to lowest chamber port 50 in slide valve 64 | Pump 55 aspirates Standard "B" from compartment 145 of pouch 33 |
| 221 | 221 |
| Probe 70 in lowest chamber port 49 of slide valve 64 | Pump 55 aspirates air through channel 148 in slide valve 64 |
| 222 | 222 |
| Probe 70 about 4" below slide valve 64 | Pump 55 aspirates sample solution from a deep container e.g. a vacutainer |
| 223 | 223 |
| Probe 70 about 1" from bottom of slide valve 64 | Pump 55 aspirates sample solution from a short container or large syringe |

The total distance travelled by probe 70 is approximately 5 inches which corresponds to 2 inches of vertical travel by cam follower pin 11.

Figure 3:
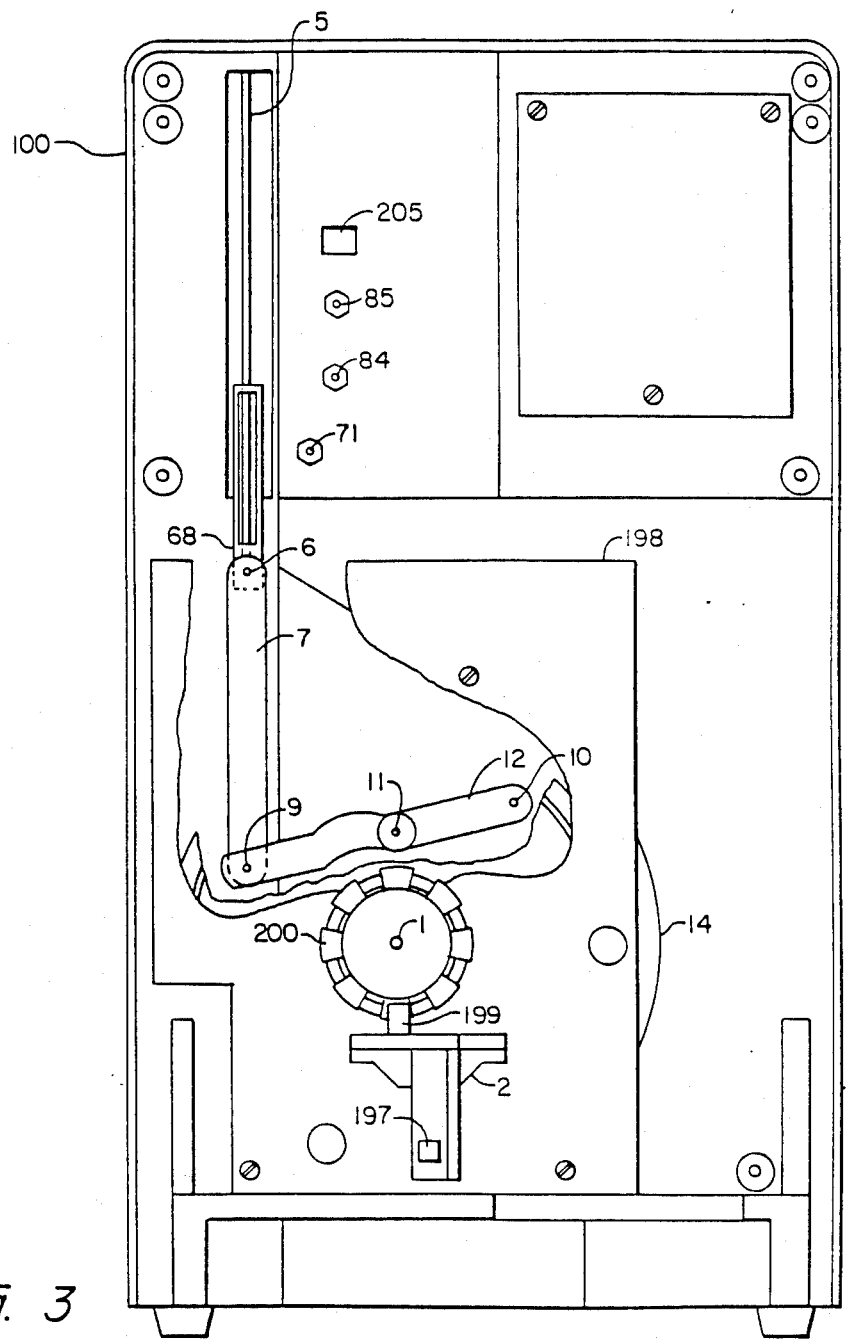
FIG. 3 is a rear elevation of the analyzer with parts broken away.
Figure 18:
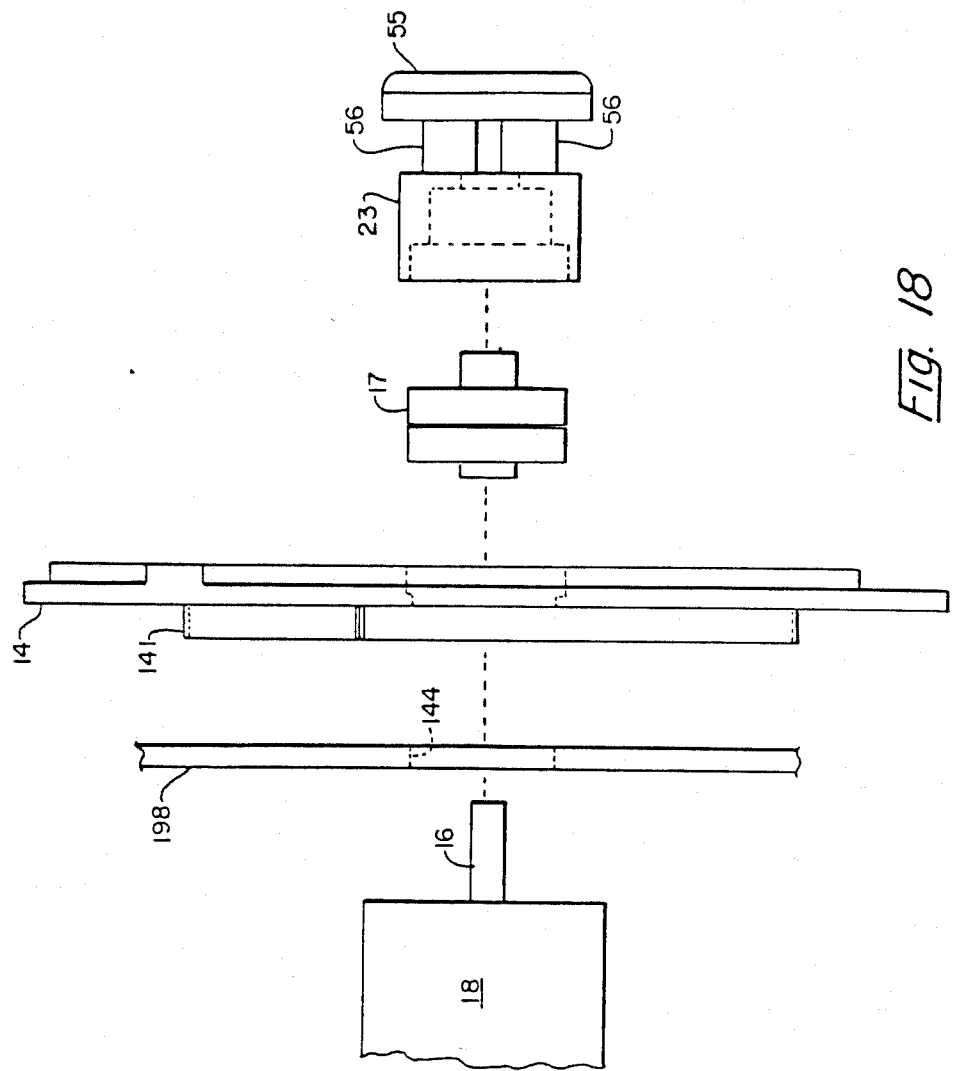
FIG. 18 is an exploded view of the drive assembly of the analyzer.

The cam drive assembly of the analyzer is illustrated in the exploded view of FIG. 18. The D.C. motor 18 is mounted on a rectangular plate 198 (FIG. 3). Its output shaft 16 passes through a hole 144 in the mounting plate 198 and is perpendicular to the mounting plate 198. The clutch 17, cam 14, and pump 55 are all on the opposite side of the mounting plate 198 from the D.C. motor 18. The mounting plate is bolted to the inside of the front half of the analyzer housing 100 which contains a hole through which pump 55 protrudes. The cam 14 is parallel to the mounting plate 198.

There are three rubber fingers 131 (FIG. 1) which are mounted on plate 198 and are disposed in between the cam 14 and mounting plate 198. They exert a slight pressure on cam 14 in the event cam 14 attempts to move backwards.

The motor 18 has an approximate 127 to 1 reduction ratio such that the cam 14 or pump 55 on the outout shaft 16 makes 1 turn for every 127 turns of the motor shaft 1. The motor shaft 1 has a slotted wheel 200 (FIG. 3) on its end which passes through an optical interrupter 199 mounted on frame assembly 2, which is also attached to the mounting plate 198. The wheel 200 contains 8 segments. The interrupter 199 keeps count of the revolutions of the motor 18. A second optical interrupter 197 is mounted on plate 198 which detects nine slits 186 (FIG. 5) on the back side of the cam 14 corresponding to the beginning of each portion of each of the nine segments which has a constant radius. The portion of each segment having a constant radius corresponds to about 3 revolutions of DC motor 18. The slits 186 operate as reference points to the nine segments as is more fully explained below.

The Electronic Control Mechanism

The computing functions of the analyzer are performed by a microprocessor based computer and other electronic components which are contained on a circuit board 196 (FIG. 1) which is mounted in the front half of analyzer housing 100. The computer and other electronic components, are powered by a power supply (not shown) in the back half of analyzer housing 100. These components are illustrated by a block diagram in FIG. 17. The electrodes, 95, 97, 98, give rise to a voltage signal when a sample solution or Standard A or B passes through their flow-through tubes. The signal is related to the activity of the potassium and sodium ions in the sample solution or reagents in accordance with the well known Nernst equation. The voltage signals are introduced into operational amplifiers 194, 195 which buffer the signal. The operational amplifiers 194, 195 have a high input impedance in comparison to the electrodes 95, 97, 98 in order to prevent too much current from being drawn through the electrodes, 95, 97, 98.

The output from the operational amplifiers 194, 195 is introduced into analog multiplexer 191. Upon receiving a programmed command from the computer 190, the multiplexer will select the output of one of the operational amplifiers 194, 195 and transmit this to A/D converter 189. The A/D converter 189 takes the analog signal which it receives and converts the difference between it and the output signal of the reference electrode 95 into a digital signal which in turn is transmitted to the computer 190. The sequencing operation of the A/D converter 189 is also controlled by the computer 190. The computer 190 determines the value of the activity of potassium and sodium ions in accordance with the Nernst equation as is explained more fully below. The results are exhibited within 60 seconds on a liquid crystal display 188.

The computer 190 also controls the mechanical functions of the analyzer. It sends signals to the solid state motor driver 187 which in turn drives D.C. motor 18. The motor driver 187 can send four signals to the D.C. motor: (1) motor forward; (2) motor reverse; (3) motor coast; (4) motor brake. The torque of the D.C. motor 18 in the motor forward or reverse modes is controlled by the number and width of the pulses outputed by the motor driver 187 pursuant to the input commands of the computer 190.

The computer 190 receives inputs from the optical interrupters 199 and 197. Optical interrupter 199 sends eight pulses for one revolution of slotted wheel 200 and hence motor shaft 1. As such, it acts as a tachometer measuring the number of revolutions of DC motor 18 to ⅛ revolutions. Optical interrupter 197 sends a pulse signal to computer 190 every time it senses one of the slits 186 in rim 141 corresponding to the nine positions of cam 14.

When the computer 190 is driving the D.C. motor 18, it sends a signal to motor driver 187 to go in the forward or reverse directions, and when it wants to stop the motor 18, it commands the motor driver 187 to go into the motor brake mode. For example, if the probe 70 is to go from port 50 of slide valve 64 to port 51 of slide valve 64 (i.e. from position No. 216 to position No. 217, on cam 14) the computer 190 will command the motor driver 187 to go into the forward mode. At the same time, the computer commences counting the number of pulses it receives from optical interrupter 199, and hence the number of revolutions of motor shaft 1. As the slit 186 in rim 141 corresponding to position No. 217 passes through optical interrupter 197, this information is received by the computer 190 which simultaneously reads the tachometer 199 and commands the motor driver 187 to go into the brake mode. It compares the tachometer 199 reading with the preset number of revolutions corresponding between position No. 216 and 217, and if the difference is greater than a set tolerance, it computes the actual cam position and continues rotating until the real position 217 is reached. 15 When the computer drives the peristaltic pump 55, it sends a command to motor driver 187 to go into the motor reverse mode. When the motor 18 starts, the computer commences countihg pulses from optical interrupter 199, and hence, the number of revolutions of motor shaft 1, and compares this information against a preset number of revolutions (corrected periodically for pump tubing stretch) corresponding to the mechanical function to be performed. For instance, when the pump 55 is to aspirate 100 mirco liters of sample solution, the pump 55 must make about 2 revolutions. When the preset number of revolutions is reached, the computer 190 signals the motor driver 187 to go into the motor brake mode.

The pumping rate, i.e. the number of microliters per revolution of pump 55, or output shaft 16 of motor 18, changes from time to time as the tubing 59 stretches with use and time. The rate is checked periodically by the computer 190 and updated to compensate for changes in the pump tubing 59. The computer 190 utilizes inputs from the bubble detector 300 in the correction procedure.

The bubble detector 300 operates as follows. Light from LED 295 (FIG. 13) passes through fiber optic 294 and out the end of cavity 296. When a sample solution or reagent passes through the flow-through tube 299 including that section 291 passing through the fiber optic 294, there is little or no change in the path of the light as the index of refraction of the fiber optic 294, about 1.4, is close to the index of refraction of water, about 1.4. Hence, no light is deflected to light detector 292. However, when a bubble or segment of air having an index of refraction of about 1.0 passes through the fiber optic 294, a significant amount of light is reflected. Some of this light is perpendicular to the axis of the fiber optic 294, and hence passes out the side of the fiber optic 294. It is sensed by the photo diode light detector 292. The output signal is introduced into an operational amplifier (not shown) which converts the low level current to a high level voltage signal. The operational amplifier also controls the LED 295 current.

The output of the operational amplifier is introduced into a differentiator (not shown) whose output operates an analog latch 142. Hence, upon the passing of an air bubble or segment, the latch 142 is tripped. It is reset each time it is read by the computer 190. The output of the detector 300 is also introduced into A/D converter 183 which in turn is introduced into computer 190. Hence, if at any time the computer reads the A/D converter 183, it will know whether an air bubble or segment is being detected by detector 300.

In the pump tube calibration procedure referred to above, the pump 55 aspirates an arbitrary volume of fluid. It then aspirates a segment of air. The computer 190 then commands the motor driver 187 to go into the motor reverse mode for the number of revolutions necessary to position the fluid such that the end of the fluid will be located at the fiber optic 294 of bubble detector 300. At the same time, the computer 190 looks for the segment of air following the fluid by monitoring latch 142 or A/D convertor 183. If the air segment is not detected, the computer 190 drives the pump 55 until the air segment is detected by the bubble detector 300. The computer 190 then compares the difference, and updates the pumping rate.

The programs for operating the analyzer are stored in the EPROMs of the computer 190. There are four operational modes; ANALYZE BLOOD?; ANALYZE URINE?; SEE LAST RESULTS?; and MAINTENANCE? Each of these modes can be selected by the operator's pressing a red (no) button 178 on the analyzer (FIG. 1) until the desired mode appears on display 188. When the desired mode appears, the operator presses a green (go) button 178. Thereafter, the operator is prompted through steps by questions and messages appearing on the display 188.

A typical cycle is illustrated by the "analyze blood" mode. Standard A is already in the fluid path. The probe 170 is positioned at the highest chamber port 52 of slide valve 64. When the operator presses the go (yes) button 178 to the question "ANALYZE BLOOD?" on the display 188, the probe 70 moves to the lowest chamber port 49 of slide valve 64 and aspirates about 20 microliters of air. The probe 70 then goes to about 4" below slide valve 64 and the question, "PROBE IN BLOOD?" appears on display 188. If the sample is in a container such as a large syringe, the operator will press the red (no) button 179 and the probe 70 will automatically go to the other sample position, 1 inch below slide valve 64.

After the probe is in the blood sample, the operator presses the green (yes) button 179, and the pump aspirates about 100 microliters of sample. The probe 70 then moves to the lowest chamber port 49 and the pump 55 aspirates about 20 microliters of air. Next, the probe 70 moves to the highest chamber port 52 and pump 55 aspirates enough Standard A (about 80 microliters) to position the sample of blood such that the trailing end of the sample is located in bubble detector 300. The computer 190 then takes reading from the electrodes 95, 97, 98. Thereafter, more Standard A is aspirated by pump 55 until a sufficient amount rinses the electrodes 95, 97, 98. The computer 190 then takes electrode readings of Standard A and compares this with its reading of Standard A prior to the cycle. If the difference is within a tolerance amount, the computer 190 sends the results of the analysis to display 188.

The computer 190 makes its calculations by comparing the potential measured in the sample with the potential measured in Standard A. Given the slope of the electrode, and concentration of Standard A, the computer can determine the concentration of potassium and sodium in the sample solution in accordance with the Nernst equation and an empirical correction curve. The slope is previously determined by the computer 190 during a calibration cycle by subtracting the potentials measured from Standard A and Standard B, the concentrations of which are both known. This calculation is performed automatically every two hours when the analyzer is in the operational mode. If the slope falls outside a predetermined range, the computer 190 sends a message to the operator via display 188 that the electrodes need replacing.

Maintenance functions are also programmed into the computer 190. For instance, 300 ul of daily wash solution from compartment 31 of pouch 32 are pumped through the system once per day to rinse and condition the sodium electrode 97. The computer 190 sends periodic maintenance messages to display 188 telling the operator when it is time to change the reagent pack 26, the electrodes, 95, 97, 98 reference membrane assembly 96, and pump tubing 59.

The present invention is not limited to the disclosed embodiment, but includes other embodiments which will occur to those skilled in the art. For instance, electrodes which sense bicarbonate, pH, lithium, calcium or other ions may be utilized in lieu of the potassium and sodium electrodes 97, 98. More than two electrodes may also be utilized in the analyzer. The inside diameters of the flow-through tubes of the bubble detector 300, potassium and sodium electrodes 97, 98 or the fluid path elements such as the sampling probe 70, the fluid path tubing 60, and pump tubing 59 may be varied depending upon the application. In the specific embodiment set forth, the inside diameters were chosen to accomodate a 100 microliter sample size of blood, serum, or plasma. The radius of the necked sections 206 of the cylindrical cavity 53 in slide valve 64 will vary depending upon the elasticity of the material of which the slide valve 64 is constructed. Elastomeric "O" rings may also be employed in lieu of the necked portions 206. The material of the slide valve itself will depend on its compatibility with the reagents and samples. Similarly, the interior dimensions and materials of the reagent pouches 32, 33 check valves 44, fitments 38, 39, tubes 37, and reagent pack 26 may vary upon the particular application. The number of pouches, fitments, and number of chamber ports in the slide valve 64 may also be varied. Other motors with different reduction ratios than DC motor 18 may also be utilized to drive the mechanical components. Similarly, variations to the cam slot 13, the mechanical link arms 7, 12 and other physical arrangements are included herein.

With respect to the bubble detector 300, different light detectors, such as photo transistors, may be utilized in lieu the photo diode 292 in which case the attendant operational amplifier may not be necessary. The shape of the cavity 291 passing through the fiber optic 294 need not be cylindrical. For example, a cavity formed as a right triangle might be used. In this case, light would be completely reflected off the hypotenuse when the cavity contains air. Other materials than the fiber optic 294 may be used as the medium containing the cavity 291. What is essential is that the medium have an index of refraction sufficiently close to blood or water such that light will not be reflected when it is incident upon the cavity. Further, the detector 292 need not be perpendicular to the incident light depending upon the material that is used for the medium and the shape of the cavity that is utilized.

We claim:

1. An analyzer for measuring the ionic values of electrolytes in a sample solution comprising:
   a. means for measuring the ionic values of electrolytes in a sample solution;
   b. a tubular sampling probe having two ends, one end being closed, a side port spaced a finite distance from the closed end, and the other end of the probe being in fluid communication with the measuring means;
   c. a slide valve a cylindrical passageway through which the probe reciprocates, the passageway having a plurality of chamber ports each of which is sealed from the other ports by the sampling probe when the sampling probe is positioned within the cylindrical passageway, each chamber port communicating with opening means on one face of the slide valve, the the plurality of opening means having a predetermined geometric pattern;
   d. a container pack containing a plurality of flexible pouches for containing reagents, each pouch having an opening containing a fitment sealed to the pouch, the pouches being disposed in the container pack with their fitments being in juxposition, the container pack having an opening in its perimeter containing and holding in place the juxtapositioned fitments, the fitments each having a connector in fluid communication with the space defined by a pouch, the connector being compatible with the openings in the slide valve and extending outwardly from the container pack in the same predetermined pattern as the openings in the slide valve, whereby the container pack can be plugged into, and unplugged from, the slide valve;

e. means for sequentially aspirating and pumping reagents contained in the pouches through the probe, the side valve, sampling probe, and the measuring means, and f. means for reciprocating the sampling probe through the passageway in the slide valve, and for sequentially locating the side port in each chamber port in the slide valve and at a finite distance outside the slide valve to aspirate a sample solution from a sample container.

2. An analyzer according to claim 1 further comprising programmable electronic computing means for controlling the sequencing of the pumping means.

3. An analyzer according to claim 1 further comprising programmable electronic computing means for controlling the timing, rate, and displacement of the reciprocating means.

4. An analyzer according to claim 1 further comprising an air segment detector for detecting air segments in the flow of sample solution or reagents, the detector being disposed between the sample probe and the measuring means.

5. An analyzer according to claim 1 wherein the slide valve contains a channel in fluid communication with the measuring means, the channel communicating with an opening on the said one face of the slide valve as the openings which communicate with the chamber ports, all the openings having a predetermined geometric pattern.

6. An analyzer according to claim 1 further comprising an air segment detector for detecting air segments in the flow of sample solution or reagents, the detector being disposed between the sample probe and the measuring means and wherein the air segment detector is comprised of:

a. a detector body having a flow-through passagway through which the sample solution and reagents flow, and having a transverse passageway in the body intersecting the flow-through passageway;

b. a fiber optic in the transverse passageway intersecting the flow-through passageway and having a flow-through channel which communicates with the flow-through passageway in the body and which forms a continuous part thereof, the flow-through channel being of a geometrical configuration such that a portion of light incident upon its perimeter surface will be reflected transversely to the fiber optic and to the flow-through channel when the flow-through channel contains air segments;

c. a light source at one end of the transverse passageway aligned with the fiber optic to project light therethrough; and d. a light detector in the body positioned transversely to the fiber optic and to the flow-through channel.

7. An analyzer according to claim 1 wherein the means for measuring comprise a plurality of flow-through ion selective electrodes and reference means.

8. An analyzer according to claim 1 wherein the means for measuring comprise a plurality of flow-through ion selective electrodes and reference means and wherein the reference means is comprised of a flow-through reference membrane assembly, reference electrode with internal filling solution, and a reservoir of the internal filling solution in fluid communication with the membrane of the reference membrane assembly and the liquid junction of the reference electrode.

9. An analyzer according to claim 1 wherein the pumping means is a peristaltic pump and pump tubing connected to the measuring means.

10. An analyzer according to claim 1 wherein the flexible pouches for containing reagents are relatively flat and of substantially equal size and volume.

11. An analyzer according to claim 1 wherein the flexible pouches have a plurality of separate sealed compartments and wherein the fitments for each pouch have a corresponding plurality of connectors in separate fluid communication with a reagent contained in each compartment of the pouch.

12. An analyzer for measuring the ionic values of electrolytes according to claim 1 wherein the means for measuring the ionic values comprise:

a. a plurality of flow-through ion selective electrodes for measuring the the ionic values of the electrolytes;

b. A flow-through reference membrane assembly;

c. means for connecting the flow-through tubes of the ion selective electrodes and the reference membrane assembly in series such that the flow-through tubes form a continuous fluid path;

d. a reference electrode; and e. a reservoir housing containing a filling solution of the internal filling solution of the reference electrode, the filling solution being in fluid communication with the reference assembly and the reference electrode.

13. An analyzer for measuring the ionic values of electrolytes according to claim 1 wherein the means for aspirating and reciprocating comprise:

a. A two-way clutch mounted on the output shaft of the motor, a peristaltic pump being mounted on one half of the clutch;

b. a probe arm having one end fixed and its other end having a pivot means;

c. means for constraining the probe arm to the direction in which the probe reciprocates through the cylindrical cavity in the slide valve;

d. a circular cam disc mounted on one half of the two-way clutch, said disc having a groove on its face that varies in distance from the center of the disc in a predetermined pattern;

e. a first link arm having one of its ends fixed and having a cam follower pin disposed in the groove of the cam disc, the link arm having a pivot means at its other end.

* * * * *